United States Patent [19]
Flower et al.

[11] Patent Number: 5,954,684
[45] Date of Patent: Sep. 21, 1999

[54] IONTOPHORETIC DRUG DELIVERY SYSTEM AND METHOD FOR USING SAME

[75] Inventors: Ronald J. Flower, Vernon, N.J.; Burton H. Sage, Jr., Raleigh, N.C.

[73] Assignee: Becton Dickinson and Company, Franklin Lakes, N.J.

[21] Appl. No.: 08/541,058

[22] Filed: Oct. 11, 1995

Related U.S. Application Data

[63] Continuation-in-part of application No. 08/129,887, Sep. 30, 1993, abandoned, and a continuation-in-part of application No. 08/129,627, Sep. 30, 1993, abandoned.

[51] Int. Cl.⁶ .................................................... A61N 1/30
[52] U.S. Cl. ................................................ 604/20; 604/49
[58] Field of Search ............................ 604/20, 290, 49; 607/149–152

[56] References Cited

U.S. PATENT DOCUMENTS

| | | | |
|---|---|---|---|
| 3,814,095 | 6/1974 | Lubens | 128/260 |
| 3,991,755 | 11/1976 | Vernon et al. | 604/20 |
| 4,019,510 | 4/1977 | Ellis | 604/20 |
| 4,141,359 | 2/1979 | Jacobsen et al. | 604/20 |
| 4,211,222 | 7/1980 | Tapper | 128/207.21 |
| 4,340,047 | 7/1982 | Tapper et al. | 604/20 |
| 4,406,658 | 9/1983 | Lattin et al. | 604/20 |
| 4,456,012 | 6/1984 | Lattin | 604/20 |
| 4,764,164 | 8/1988 | Sasaki | 604/20 |
| 4,786,278 | 11/1988 | Masaki | 604/20 |
| 4,820,263 | 4/1989 | Spevak et al. | 604/20 |
| 4,822,334 | 4/1989 | Tapper | 604/20 |
| 4,927,408 | 5/1990 | Haak et al. | 604/20 |
| 4,950,229 | 8/1990 | Sage, Jr. | 604/20 |
| 5,006,108 | 4/1991 | LaPrade | 604/20 |
| 5,047,007 | 9/1991 | McNichols et al. | 604/20 |
| 5,084,008 | 1/1992 | Phipps | 604/20 |
| 5,088,977 | 2/1992 | Sibalis | 604/20 |
| 5,135,478 | 8/1992 | Sibalis | 604/20 |
| 5,160,316 | 11/1992 | Henley | 604/20 |
| 5,221,254 | 6/1993 | Phipps | 604/20 |
| 5,224,927 | 7/1993 | Tapper | 604/20 |
| 5,246,418 | 9/1993 | Haynes et al. | 604/20 |
| 5,256,137 | 10/1993 | Sage, Jr. | 604/20 |

*Primary Examiner*—Mark Bockelman
*Attorney, Agent, or Firm*—Royal N. Ronning, Jr.; Susan A. Capello

[57] ABSTRACT

An iontophoretic drug delivery device of the present invention includes a power source and an electrode assembly containing at least two electrodes, in electrical contact with a first reservoir and a second reservoir. The present invention also includes at least three electrodes in a three electrode embodiment, with the third electrode in electrical contact with a third reservoir. In either embodiment, the first reservoir and the second reservoir contain an active agent to be delivered to an applied area of a patient. The present invention also includes in its two electrode embodiment a switch for reversing the flow of current or in its three electrode embodiment a switch for switching the flow of current, so as to reduce sensation. The devices also include a timer for controlling the amount of time the electrical current flows in each direction. In this way, the devices are suitable for use to deliver an active agent to the applied area approximate the first reservoir when the electrical current flows in one direction for a first period of time and to deliver an active agent to the applied area approximate the second reservoir when the electrical current flows in the other direction during a second period of time. Thus, reversing polarity or switching the flow of current between electrodes, and iontophoresing thereunder below the sensation threshold results in sensation anesthesia so that the current can be raised to deliver the drug without sensation.

9 Claims, 20 Drawing Sheets

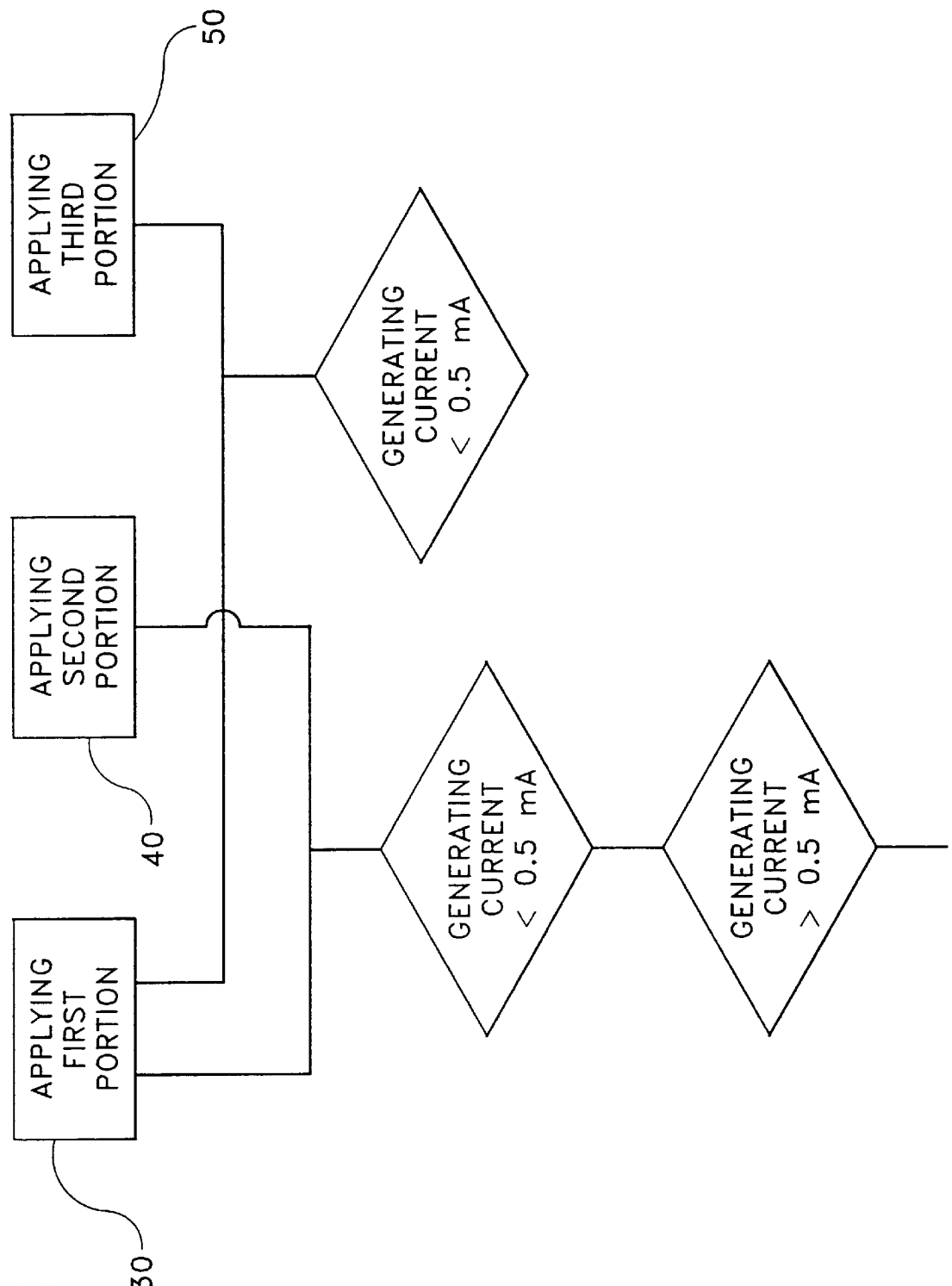

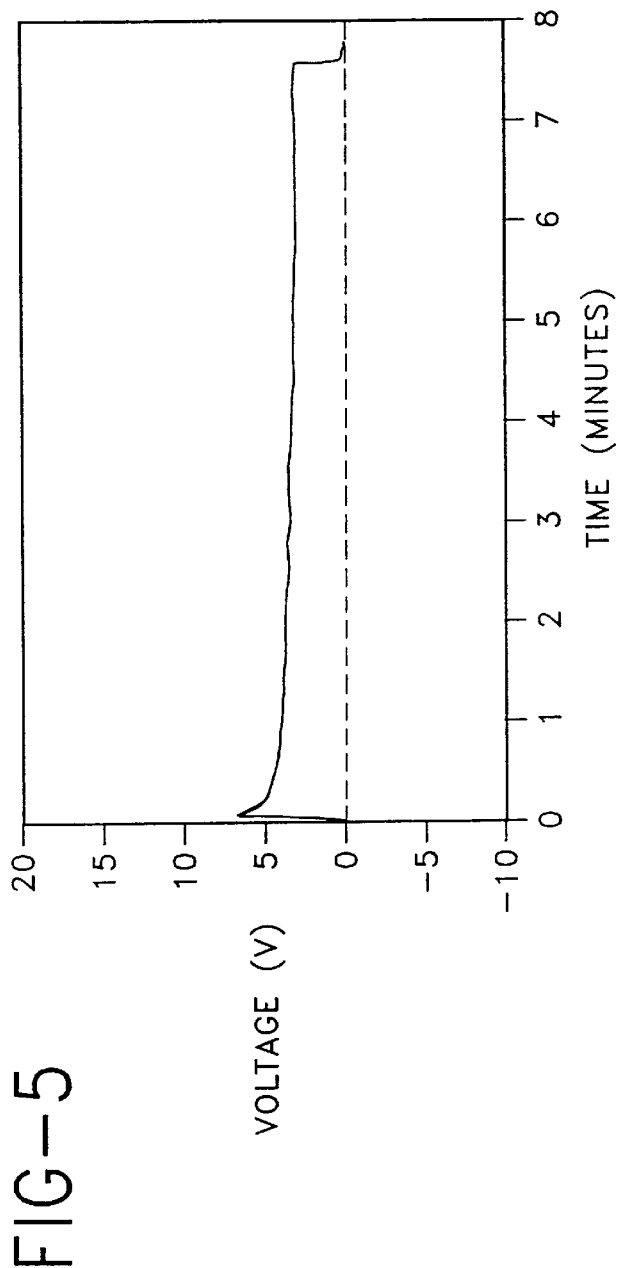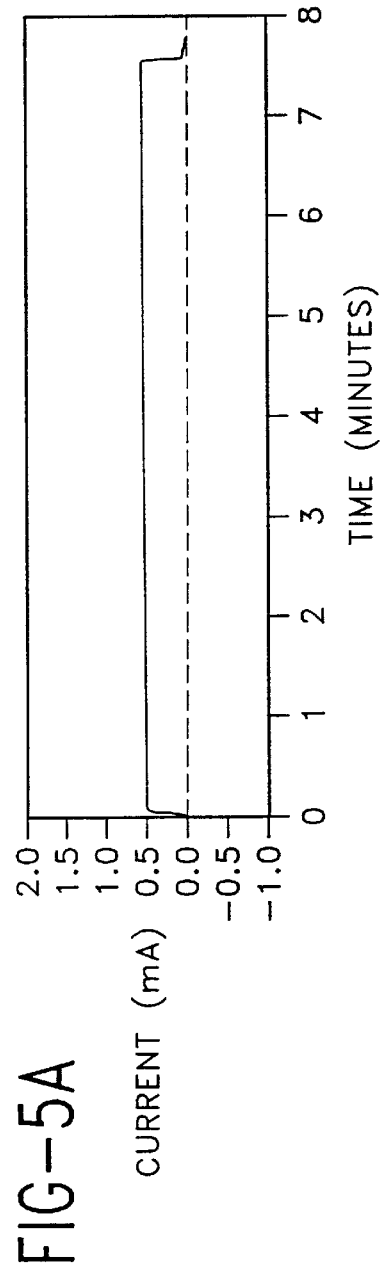
FIG-5
FIG-5A

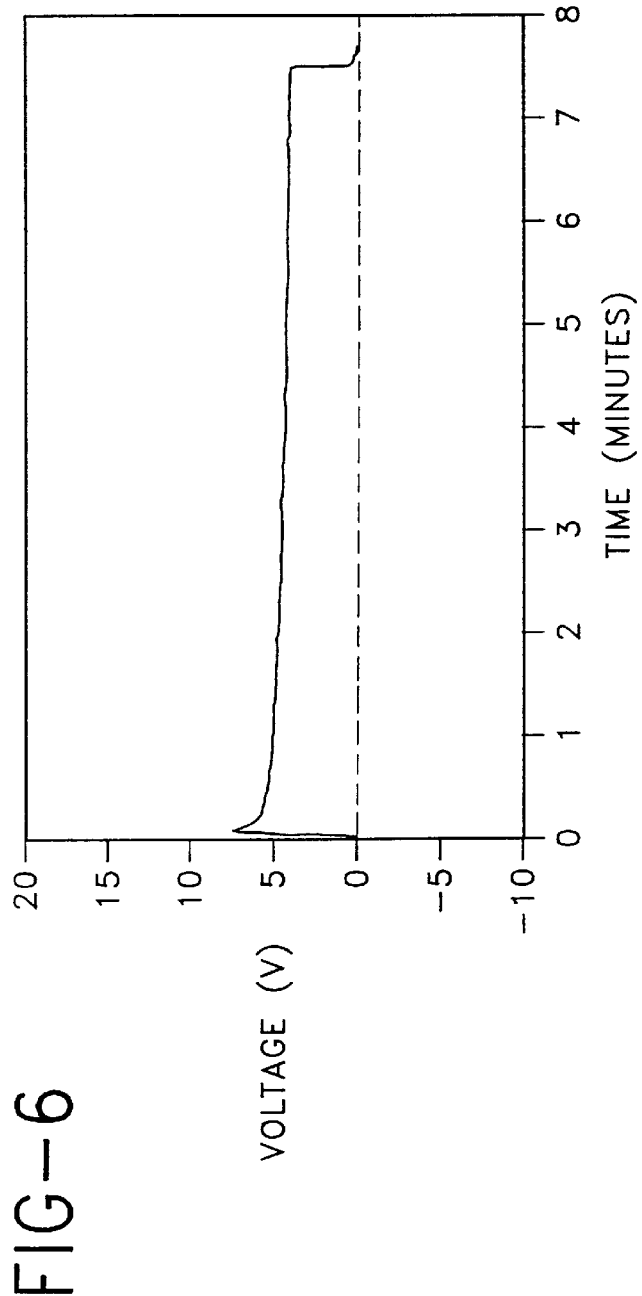
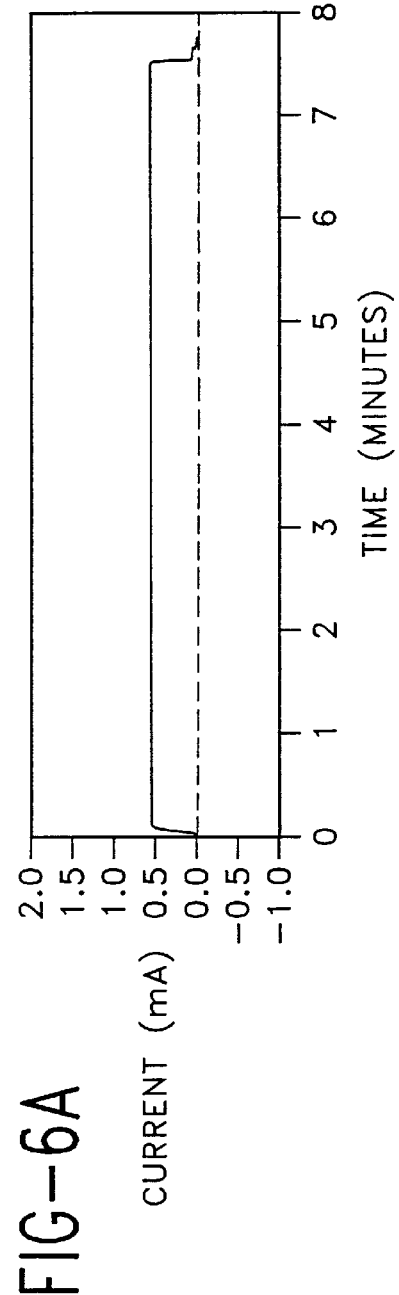
FIG-6
FIG-6A

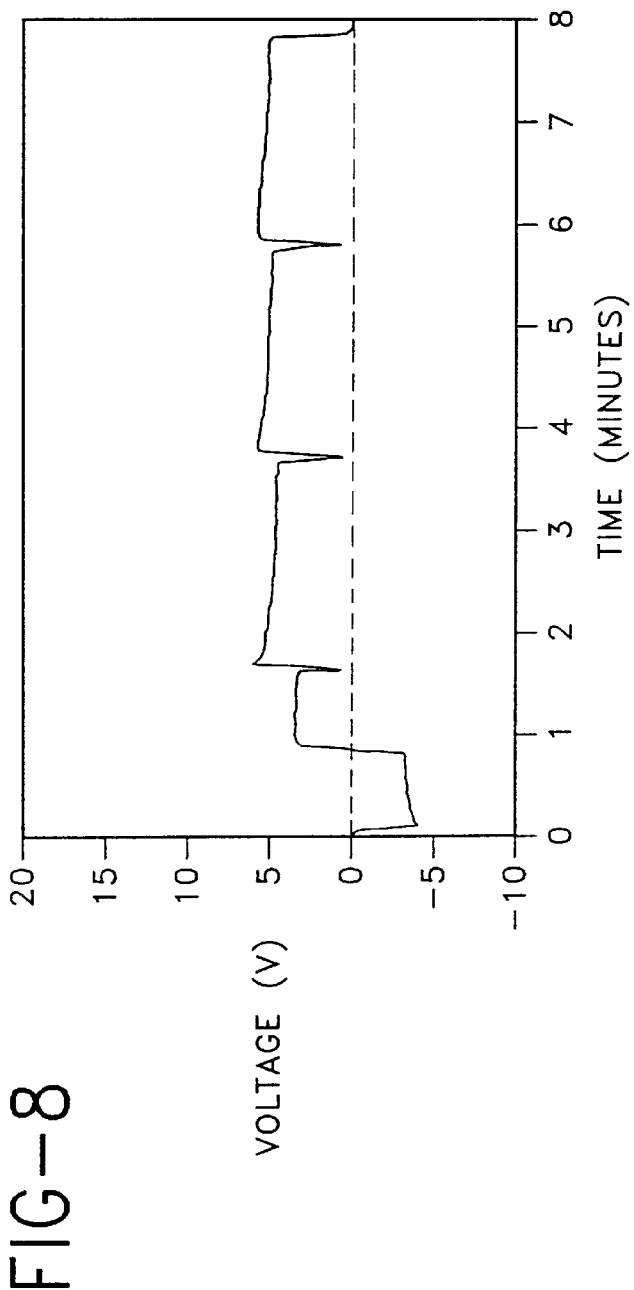
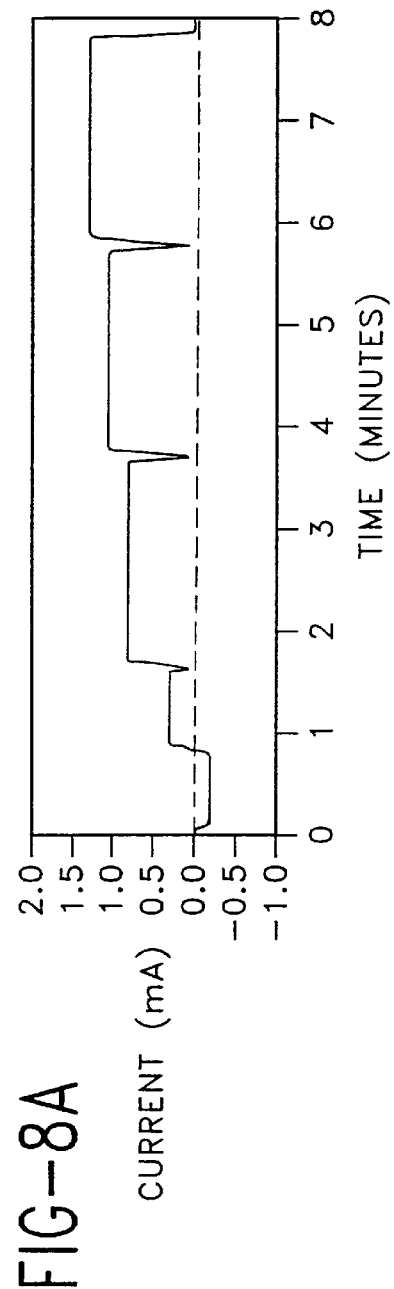
FIG-8
FIG-8A

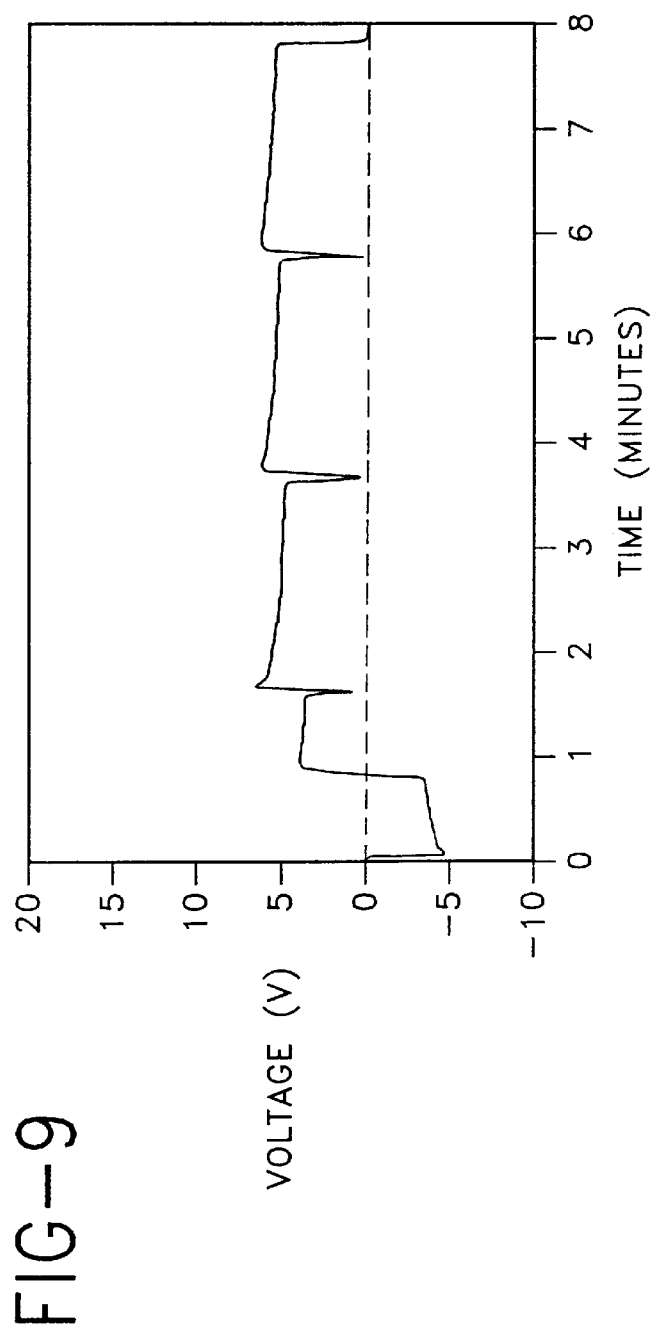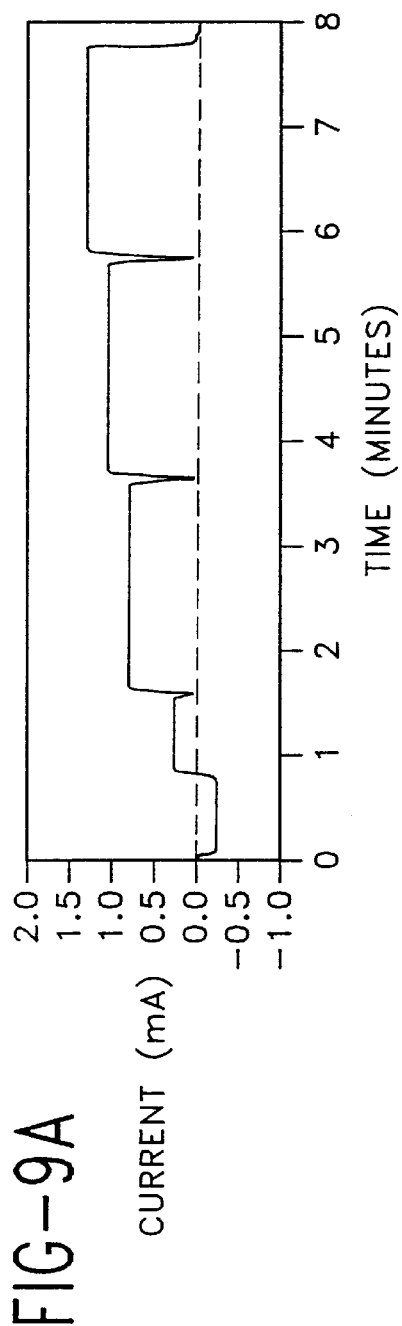
FIG-9
FIG-9A

IONTOPHORETIC DRUG DELIVERY SYSTEM AND METHOD FOR USING SAME

This application is a continuation in part of application Ser. No. 08/129,887 filed Sep. 30, 1993 now abandoned and continuation in part of Ser. No. 08/129,627 filed Sep. 30, 1993 now abandoned.

FIELD OF THE INVENTION

The present invention generally relates to iontophoretic devices for delivering drugs or medicines to patients transdermally, i.e., through the skin, and more specifically relates to a drug delivery device with polarity reversal for anesthetizing an area. In addition, the present invention relates to a method for anesthetizing an area using the iontophoretic drug delivering device.

BACKGROUND OF THE INVENTION

Transdermal drug delivery systems have, in recent years, become an increasingly important means of administering drugs. Such systems offer advantages clearly not achievable by other modes of administration such as avoiding introduction of the drug through the gastrointestinal tract or punctures in the skin to name a few.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using iontophoresis, which according to Stedman's Medical Dictionary, is defined as "the introduction into the tissues, by means of an electric current, of the ions of a chosen medicament."

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, i.e., an anode and a cathode. Usually, electric current is driven from an external supply into the skin at the anode, and back out at the cathode. Accordingly, there has been considerable interest in iontophoresis to perform delivery of drugs for a variety of purposes.

However, several disadvantages and limitations have been associated with the use of such devices, including unacceptable levels of sensations due to current flow during iontophoresis, which in severe cases can be painful.

Attempts to reduce or mitigate such unacceptable levels of sensation have included employing materials between the electrode and the patient's skin as disclosed in U.S. Pat. No. 4,211,22 (Tapper), gradually imposing the current as disclosed in U.S. Pat. No. 4,340,047 (Tapper), pulsating the voltage as disclosed in U.S. Pat. No. 4,764,164 (Sasaki), reducing the current prior to switching polarity as disclosed in U.S. Pat. No. 4,406,658 (Lattin et al.), and alternating between biphasic stimulation and iontophoretic delivery as disclosed in U.S. Pat. No. 4,456,102 (Lattin), the disclosures of which are hereby incorporated by reference. Nevertheless, despite such attempts unacceptable sensation levels remain, especially when drug is delivered with high efficiency.

In addition to the above, amounts of a multivalent ion such as calcium, magnesium, phosphate and zinc have been included in the drug reservoir to reduce sensation as disclosed in U.S. Pat. No. 5,221,254 (Phipps), the disclosure of which is hereby incorporated by reference. However, the presence of such multivalent ions competes with the agent to be delivered and reduces the overall effect.

Specifically, unacceptable sensation levels have even been encountered during the iontophoretic delivery of local anesthetics, especially when rapid onset of the local anesthetic is desired involving, for example, the use of Novocaine, which is usually injected prior to dental work to relieve pain or the use of Lidocaine, which is usually applied as a topical, local anesthetic as disclosed in U.S. Pat. No. 4,950,229 (Sage, Jr. et al.), the disclosure of which is hereby incorporated by reference.

Thus, there has been a need for an iontophoretic drug delivery device, as well as a method for reducing skin pain, which would eliminate the problems and limitations associated with the prior devices discussed above, most significant of the problems being unacceptable levels of sensation. In addition, there has been a need for a device, which would reduce sensation without affecting the overall effect of the agent to be delivered.

SUMMARY OF THE INVENTION

In contrast to the prior devices discussed above, it has been found that a iontophoretic drug delivery device particularly suited for use in reducing or otherwise eliminating sensation can be constructed in accordance with the present invention. In addition, the device of the present invention does not compete with the agent to be delivered, which for example in the case of skin pain relief, does not reduce the overall anesthesia.

The iontophoretic drug delivery device of the present invention for delivering at least one active agent to an applied area of a patient, such as the skin, mucus membrane and the like, includes power means for supplying a source of electrical current, electrode assembly means including at least two electrodes for driving the at least one active agent into the applied area of the patient along electrical field lines generated by the electrical current, a first reservoir situated in electrical communication with one of the electrodes and the first reservoir containing the at least one active agent to be delivered to the applied area of the patient, a second reservoir situated in electrical communication with the other one of the electrodes and the second reservoir containing the at least one active agent to be delivered to the applied area of the patient, and means for reversing the flow of the electrical current between a first direction along the field lines during a first period of time and a second direction along the field lines during a second period of time, so that the at least one active agent is delivered to the applied area of the patient approximate the first electrode during the first period of time and the at least one active agent is delivered to the applied area of the patient approximate the second electrode during the second period of time to eliminate unwanted sensation due to electrical current flowing through the applied area of the patient; wherein the current reversal sequence may be repeated as desired.

In a three electrode embodiment of the present invention, the iontophoretic drug delivery device includes an electrode assembly means including at least three electrodes for driving the at least one active agent into the applied area of the patient along electrical field lines generated by the electrical current, a first reservoir situated in electrical communication with a first one of the electrodes and the first reservoir containing the at least one active agent to be delivered to the applied area of the patient, a second reservoir situated in electrical communication with a second one of the electrodes and the second reservoir containing the at least one active agent to be delivered to the applied area of the patient, a third reservoir situated in electrical communication with a third one of the electrodes, and means for switching the flow of the electrical current from between the first electrode and third electrode along the field lines during a first period of time and between the first electrode and the second electrode along electric field lines during a second period of time, so that the at least one active agent is delivered to the applied area of the patient approximate the first reservoir during the first period of time and the at least one active agent is delivered to the applied area of the patient approximate the second reservoir during the second period of time; wherein the current switching sequence may be repeated as desired.

In the preferred embodiments of the iontophoretic drug delivery devices, the at least one active agent includes a local anesthetic and a vasoconstrictor, with the local anesthetic being Lidocaine and the vasoconstrictor being Epinephrine. Also, the iontophoretic drug delivery devices includes timing means for controlling the means for reversing or switching the electrical current, with the timing means adapted so that the first and second time periods are preferably equal. In addition, the iontophoretic drug delivery device includes means for controlling the amount of electrical current.

The method for the two electrode embodiment of the present invention for reducing sensation during iontophoretically delivering at least one active agent to an applied area of a patient such as the skin, mucus membrane or the like, includes the steps of applying a first portion of an iontophoretic drug delivery device including an electrode assembly having a first electrode and a first reservoir containing at least one active agent to be delivered to the applied area of the patient, applying a second portion of the device including the electrode assembly having a second electrode and a second reservoir containing the at least one active agent to be delivered to the applied area of the patient, generating an electrical current between the first electrode and the second electrode through the applied area of the patient in a first direction during a first period of time so that the at least one active agent is delivered to the applied area of the patient approximate the first electrode and the first reservoir during the first period of time, and reversing the direction of the electrical current through the applied area of the patient in a second direction and generating an electrical current between the second electrode and the first electrode during a second period of time so that the at least one active agent is delivered to the applied area of the patient approximate the second electrode during the second period of time to eliminate unwanted sensation due to electrical current flowing through the applied area of the patient.

The method for the three electrode embodiment of the present invention includes the steps of applying a first portion of an iontophoretic drug delivery device including an electrode assembly having a first electrode and a first reservoir containing at least one active agent to be delivered to the applied area of the patient, applying a second portion of the device including the electrode assembly having a second electrode and a second reservoir containing the at least one active agent to be delivered to the applied area of the patient, applying a third portion of the device including the electrode assembly having a third electrode and a third reservoir, generating an electrical current between the first electrode and the third electrode through the applied area of the patient during a first period of time so that the at least one active agent is delivered to the applied area of the patient approximate the first electrode and the first reservoir during the first period of time, and generating an electrical current between the first electrode and the second electrode through the applied area of the patient during a second period of time so that the at least one active agent is delivered to the applied area of the patient approximate the second electrode and the second reservoir during the second period of time.

In a preferred embodiment of the methods of reducing sensation, the at least one active agent includes a local anesthetic and a vasoconstrictor, with the local anesthetic being Lidocaine and the vasoconstrictor being Epinephrine. Also, the methods includes the step of varying the period of time so that the first period of time is less than the second period of time and includes the step of varying the amount of electrical current.

In addition, in the preferred method of the two electrode embodiment, the step of generating an electrical current in the first direction during the first period of time includes limiting the amount of electrical current delivered to at least initially less than or equal to 0.5 mA., and the step of generating electrical current in the second direction during the second period of time includes limiting the amount of electrical current delivered to at least initially less than or equal to 0.5 mA.

In the preferred method of the three electrode embodiment, the step of generating an electrical current during the first period of time includes limiting the amount of electrical current delivered to at least initially less than or equal to 0.5 mA., and the step of generating electrical current during the second period of time includes limiting the amount of electrical current delivered to at least initially less than or equal to 0.5 mA.

Also, the preferred method of the two electrode embodiment includes the step of generating an electrical current in the second direction for at least one additional period of time during which the amount of electrical current delivered is in the range of approximately 0.05 mA to 1.5 mA. Similarly, the preferred method of the three electrode embodiment includes the step of generating an electrical current between the first electrode and the second electrode for at least one additional period of time during which the amount of electrical current delivered is in the range of approximately 0.05 mA to 1.5 mA.

The iontophoretic drug delivery device of the present invention in its two electrode embodiment for delivering a local anesthetic to an applied area of a patient, such as the skin, mucus membrane and the like, includes power means for supplying a source of electrical current, electrode assembly means including at least two electrodes for driving the local anesthetic into the applied area of the patient along electrical field lines generated by the electrical current, a first reservoir situated in electrical communication with one of the electrodes and the first reservoir containing the local anesthetic to be delivered to the applied area of the patient, a second reservoir situated in electrical communication with the other one of the electrodes and the second reservoir containing the local anesthetic to be delivered to the applied area of the patient, means for reversing the flow of the electrical current between a first direction along the field lines during a first period of time and a second direction along the field lines during a second period of time, so that the local anesthetic is delivered to the applied area of the patient approximate the first electrode during the first period of time and the local anesthetic is delivered to the applied area of the patient approximate the second electrode during the second period of time to eliminate unwanted sensation due to electrical current flowing through the applied area of the patient, and means for varying the amount of the electrical current and the amount of voltage.

The iontophoretic drug delivery device in its three electrode embodiment, includes power means for supplying a source of electrical current, electrode assembly means including at least three electrodes for driving the local anesthetic formulation into the applied area of the patient along electrical field lines generated by the electrical current, a first reservoir situated in electrical communication with a first one of the electrodes and the first reservoir containing the local anesthetic formulation to be delivered to the applied area of the patient, a second reservoir situated in electrical communication with a second one of the electrodes and the second reservoir containing the local anesthetic formulation to be delivered to the applied area of the patient, a third reservoir situated in electrical communication with a third one of the electrodes, means for switching the flow of the electrical current between the first electrode and the third electrode along the field lines during a first period of time and between the first electrode and the second electrode along the field lines during a second period of time, so that the local anesthetic formulation is delivered to the applied area of the patient approximate the first electrode during the first period of time and the local anesthetic formulation is delivered to the applied area of the patient approximate the second electrode during the second period of time to eliminate unwanted sensation due to electrical current flowing through the applied area of the patient, and means for varying the amount of the electrical current and the amount of voltage.

In the preferred embodiments of the iontophoretic drug delivery devices, the local anesthetic formulation includes a vasoconstrictor, with the local anesthetic formulation including Lidocaine and the vasoconstrictor being Epinephrine. In addition, the Lidocaine is in the range of 5% w/v–15% w/v and Epinephrine is in the range of 0.03% w/v–3.0% w/v.

BRIEF DESCRIPTION OF THE DRAWINGS

The various features, objects, benefits, and advantages of the present invention will become more apparent upon reading the following detailed description of the preferred embodiments along with the appended claims in conjunction with the drawings, wherein like reference numerals identify corresponding components, and:

FIGS. 3, 3A and 3B are block diagrams depicting the various steps of the devices of the present invention;

FIGS. 5, 5A, 5B, 6, 6A and 6B are sets of graphs showing baseline current sensation of the two electrode embodiment of the present invention wherein the Voltage (V) is on the average at about 5 volts and the Current is set at 0.5 mA;

FIGS. 8, 8A, 8B, 9, 9A and 9B are sets of graphs showing sensation of the two electrode embodiment of the present invention wherein the Current is reversed after an initial period of time (minutes) and the Voltage (V) is on the average about 5 volts and the Current is then increased to values higher than 0.5 mA.

DETAILED DESCRIPTION OF THE PREFERRED EMBODIMENT

Figure 1:
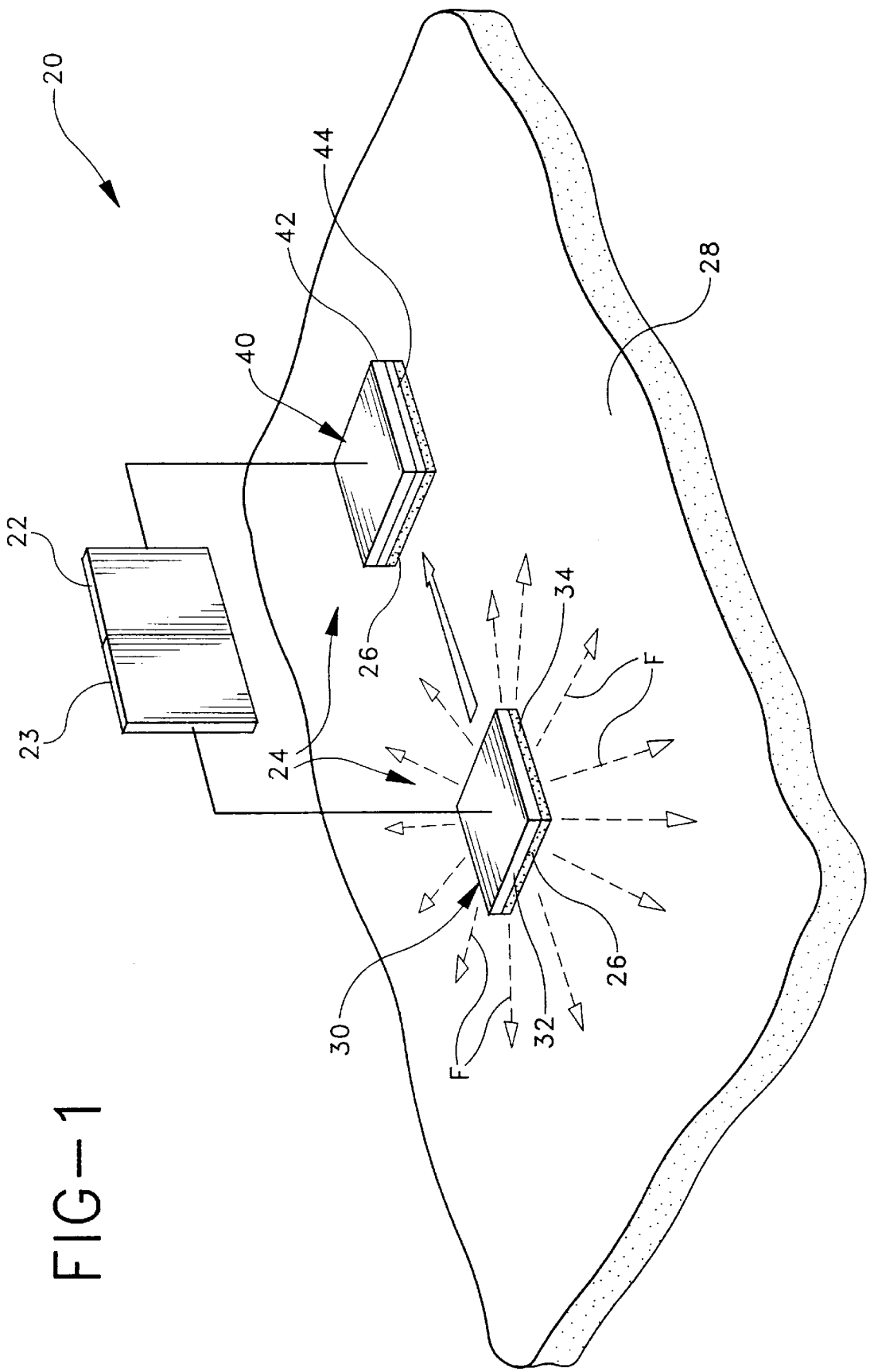
FIGS. 1 and 1A are schematic elevational views of the two embodiments of the iontophoretic drug delivery devices of the present invention illustrating connection of the electrode assembly to circuitry for driving the active ingredient into the skin of an animal.

The iontophoretic drug delivery devices of the present invention are illustrated in FIGS. 1, 1A, 2, 2A, 2B, 3, 3A and 3B, and generally includes the designation 20. Referring to FIGS. 1, 1A, 2 and 2B, the device 20 of the present invention includes a controller 22 and a power source 23 electrically connected to an electrode assembly 24 having one or more electrodes for establishing electric field lines F having lines of energy between the electrodes for use in delivering at least one active agent 26 iontophoretically to an applied area of the patient 28. It should be appreciated that the electrodes may be combined in the assembly 24 or separately provided as is well known in the art.

In the preferred two electrode embodiment, the electrode assembly is divided or otherwise separated into at least two portions, one portion 30 (first) includes the electrode 32 and the reservoir 34, with the reservoir being situated adjacent to and in electrical communication with the electrode, the second portion 40 (second) also includes an electrode 42 and a reservoir 44, with the reservoir being situated adjacent to and in electrical communication with the electrode.

In the preferred three electrode embodiment, the electrode assembly further includes a third portion 50 which includes the electrode 52 and a reservoir 54, with the reservoir being situated adjacent to and in electrical communication with the electrode.

In either preferred embodiment, both the first reservoir 34 and the second reservoir 44 hold the active agent, formulation, medication or drug 26, preferably in an ionized or ionizable form, to be delivered iontophoretically to the applied area of the patient. The electrodes 32, 42 and 52 may include an electrolyte, with the particular electrolyte not being essential to the present invention and merely a matter of choice. However, in this embodiment the electrolyte may include sodium chloride in an aqueous solution, matrix or the like, including water soluble polymer materials, with the polymer materials also including a structurally reinforcing member situated therein. In situations where a polymer material or another material is used, it may also act as an adhesive, eliminating the need in prior devices for an adhesive layer or the like.

Referring to FIGS. 1A, 2A, 3 or 3A, the controller 22 and the power source 23, such as for example a battery, are connected in a circuit, with the controller 22 preferably including a microprocessor, a dc/dc converter to increase the battery supply to approximately 30 volts, a current regulator which is controlled by the microprocessor and a switch 56, or a switch 66, for switching the direction of the electrical current, and a timer 58, or a timer 68, for monitoring the period of time the electrical current flows in a particular direction. In this way, the current flowing through the reservoirs 34, 44, 54 and the applied area 28 can be controlled with a compliance voltage sufficient to account for variations in skin impedance and losses within the reservoirs. In the preferred embodiments, the controller 22 includes means for controlling the level of current to be applied over time and also for varying the current. Accordingly, the device 20 can be utilized, for example, to vary the current $I_1$ during time period $T_1$, current $I_2$ during time period $T_2$, current $I_3$ during time period $T_3$, current $I_4$ during time period $T_4$, and current $I_5$ during time period $T_5$ and additional currents and time intervals as needed. Also, the controller may be adapted to include means for controlling the voltage V or the power I·V as well.

As is well known within the field, the device can be situated on the area of the patient to which the active agent is to be applied (the applied area) such as the skin and a voltage impressed across the electrodes of the electrode assembly 24 to cause electrical current to flow through the skin 28 of the patient to drive or otherwise transport the ionic active agent into the skin and the tissue along the field lines F to be absorbed by the body of the patient. The electric field lines F are sufficiently long, however, so that the active agent is transported to the desired depth within the skin, and possibly to the vasculature, to provide the desired effect, e.g., anesthetic, therapeutic or diagnostic. It should also be appreciated that the device of the present invention can be applied to other areas of the body such as mucus membranes depending upon the desired therapy and drugs to be delivered.

The active agent can have either a negative charge or a positive charge, but the active electrode must also be negatively or positively charged, respectively. Accordingly, in the two electrode embodiment of the present invention, where the active agent contained in the reservoirs 34, 44 is positively charged, the electrical current flows from the first electrode 32 to the second electrode 42 during a first time period and the first electrode 32 acts as the active electrode and the second electrode 42 acts as the return electrode, with the drug 26 being delivered to the applied area of the skin approximate the first electrode 32 and first reservoir 34.

Figure 1A:
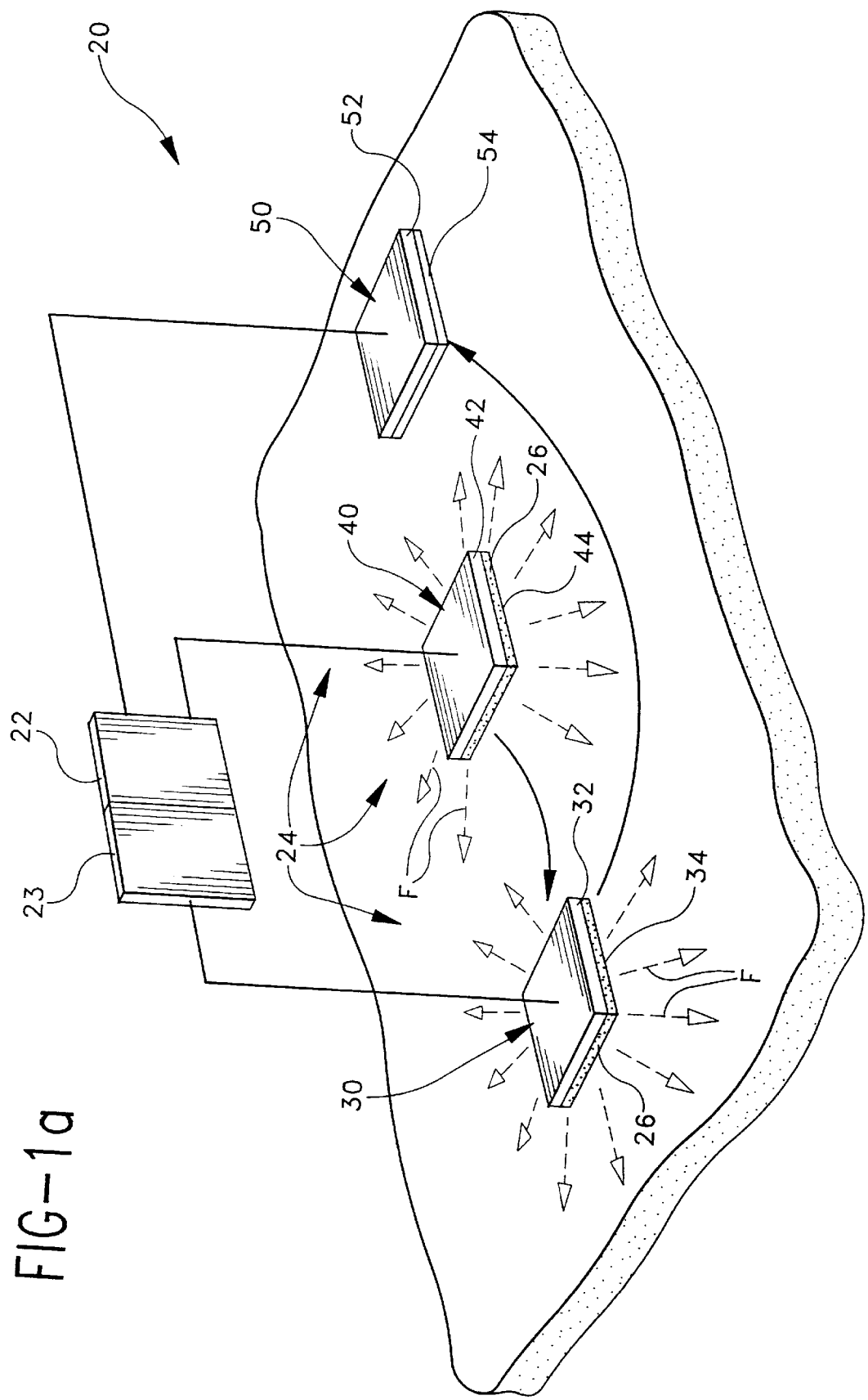
Figure 2:
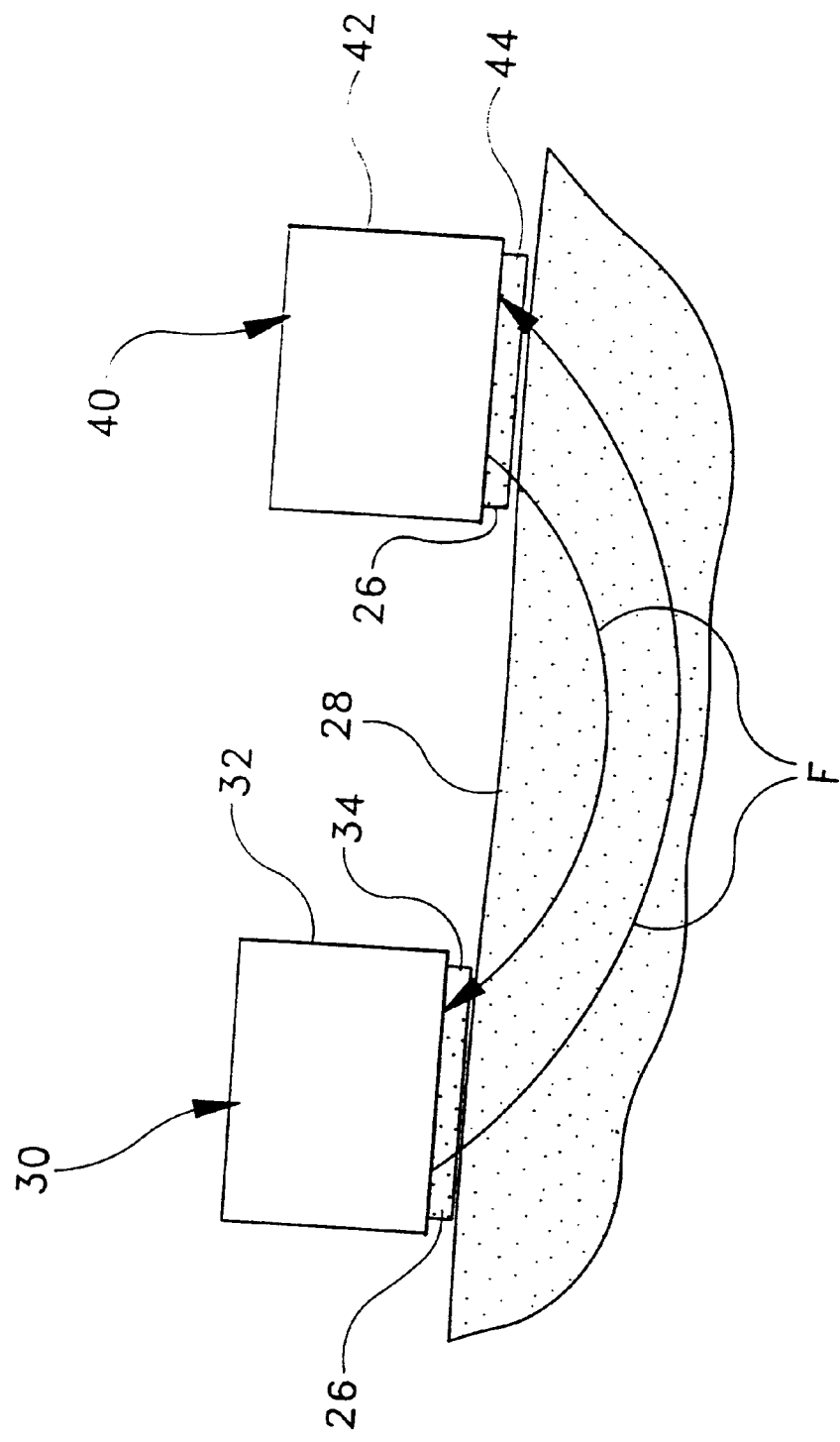
FIGS. 2, 2A and 2B are schematic, cross sectional views of the devices of the present invention illustrated in FIGS. 1 and 1A showing the direction of the current during delivery of the active ingredient.
Figure 2A:
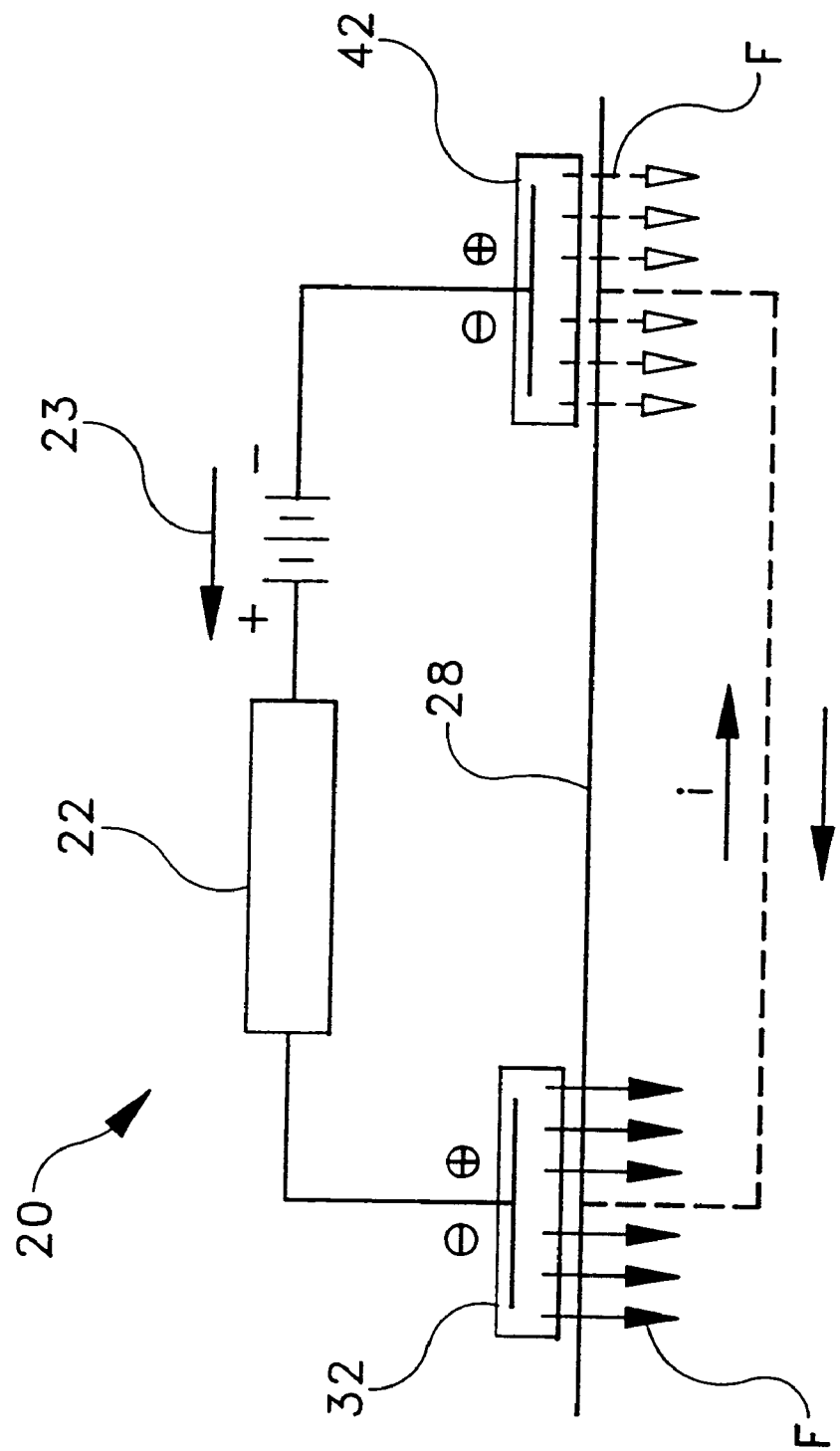
Figure 2B:
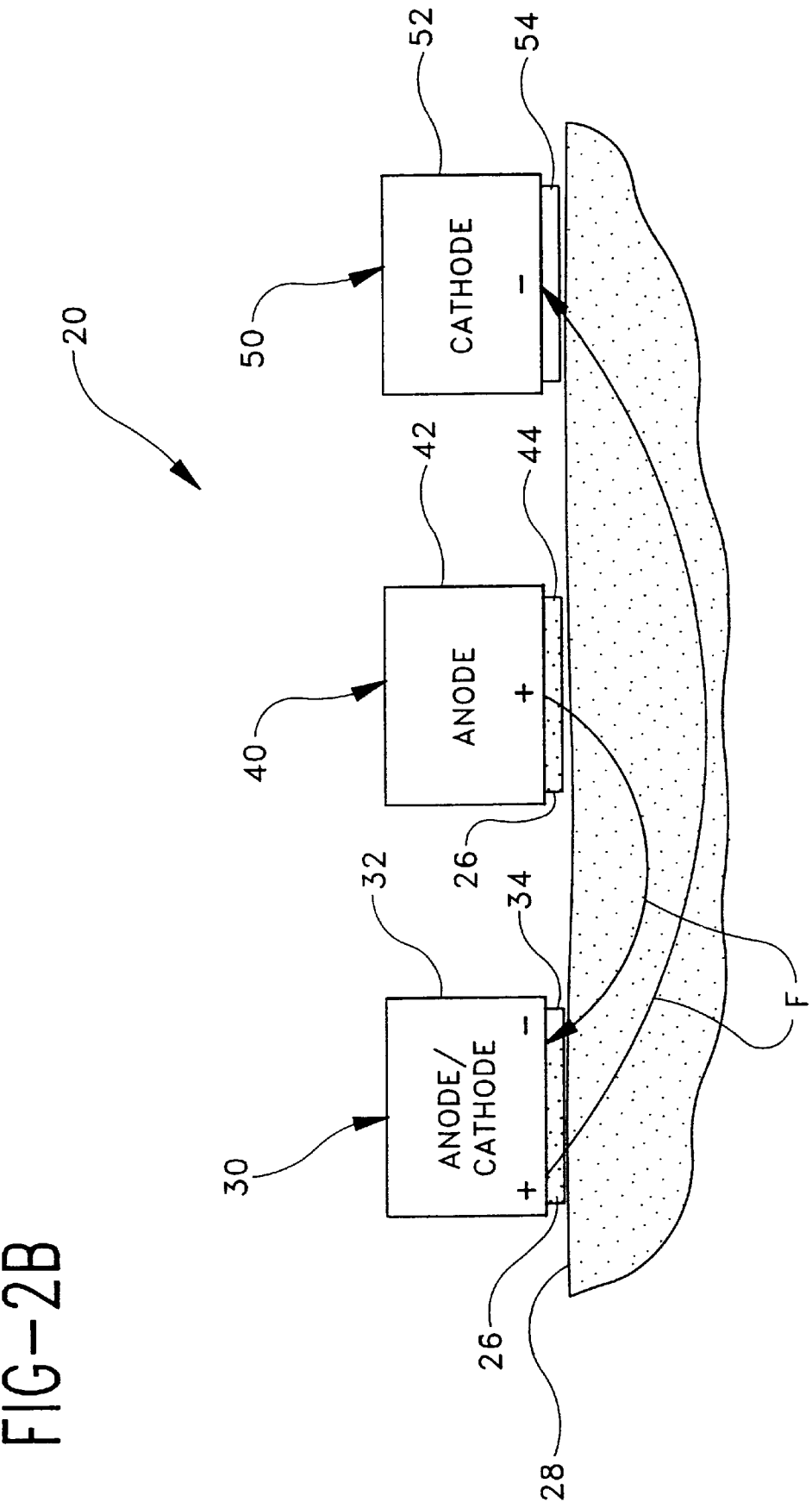
Figure 3:
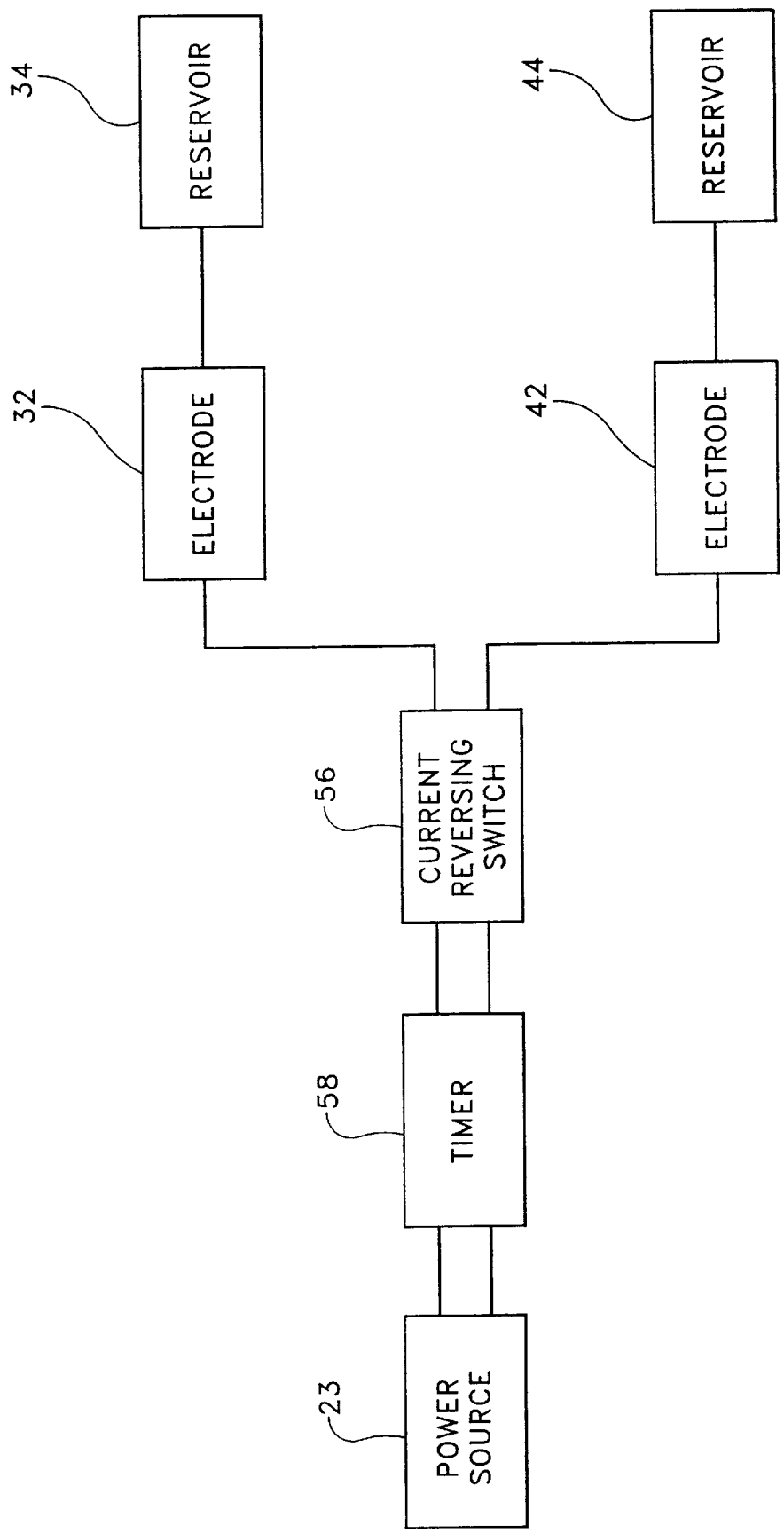
Figure 3A:
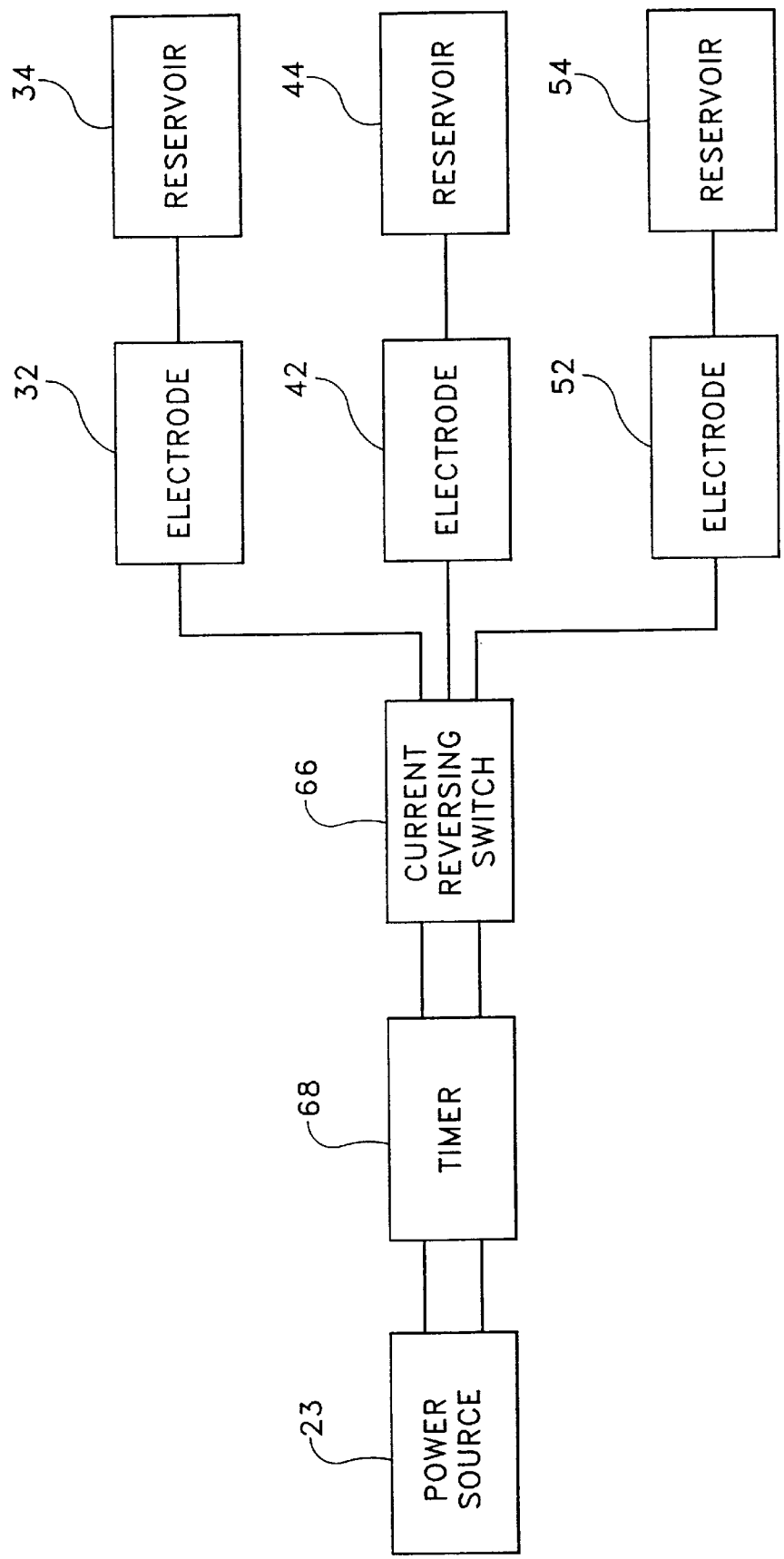
Figure 4:
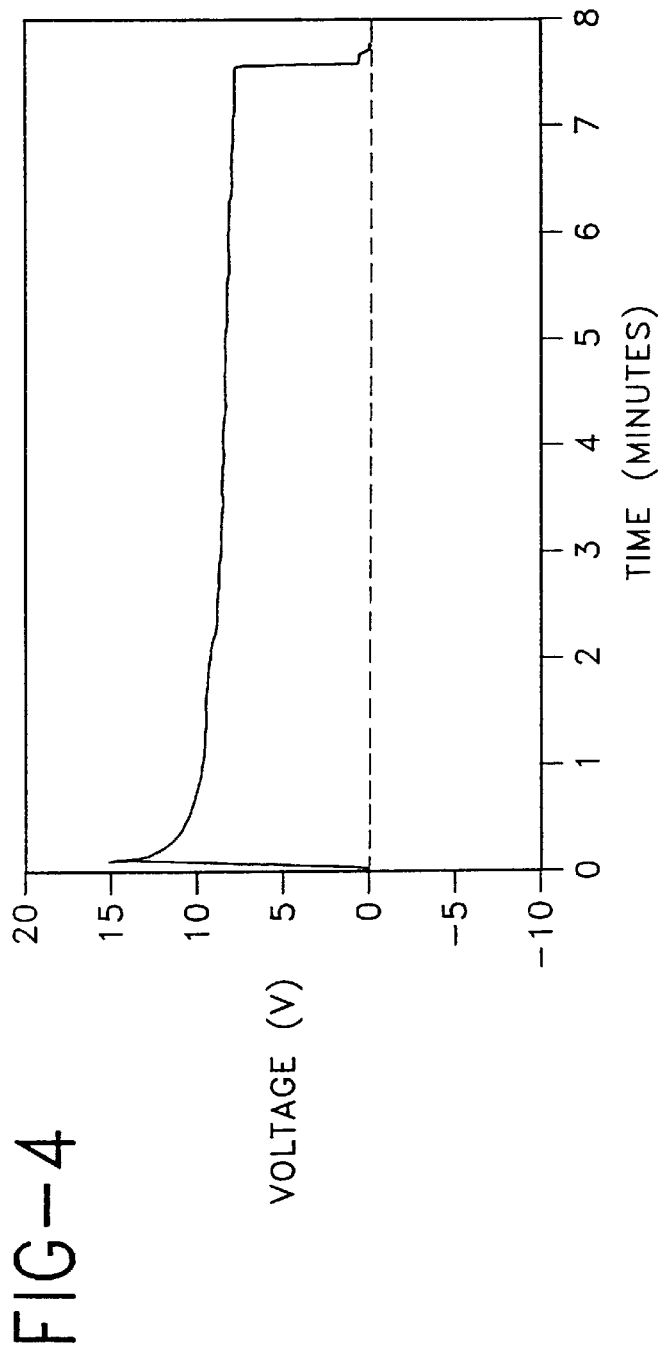
FIGS. 4, 4A and 4B are a set of graphs showing baseline current sensation of the two electrode embodiment of the present invention wherein the Voltage (V) is maintained on the average at about 10 volts and the Current is set at 0.5 mA.
Figure 4A:
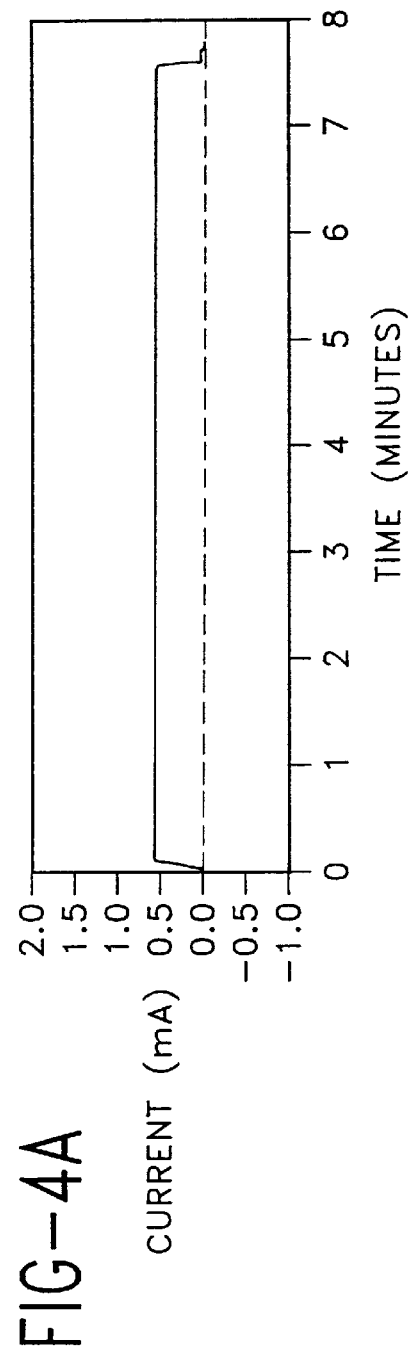
Figure 4B:
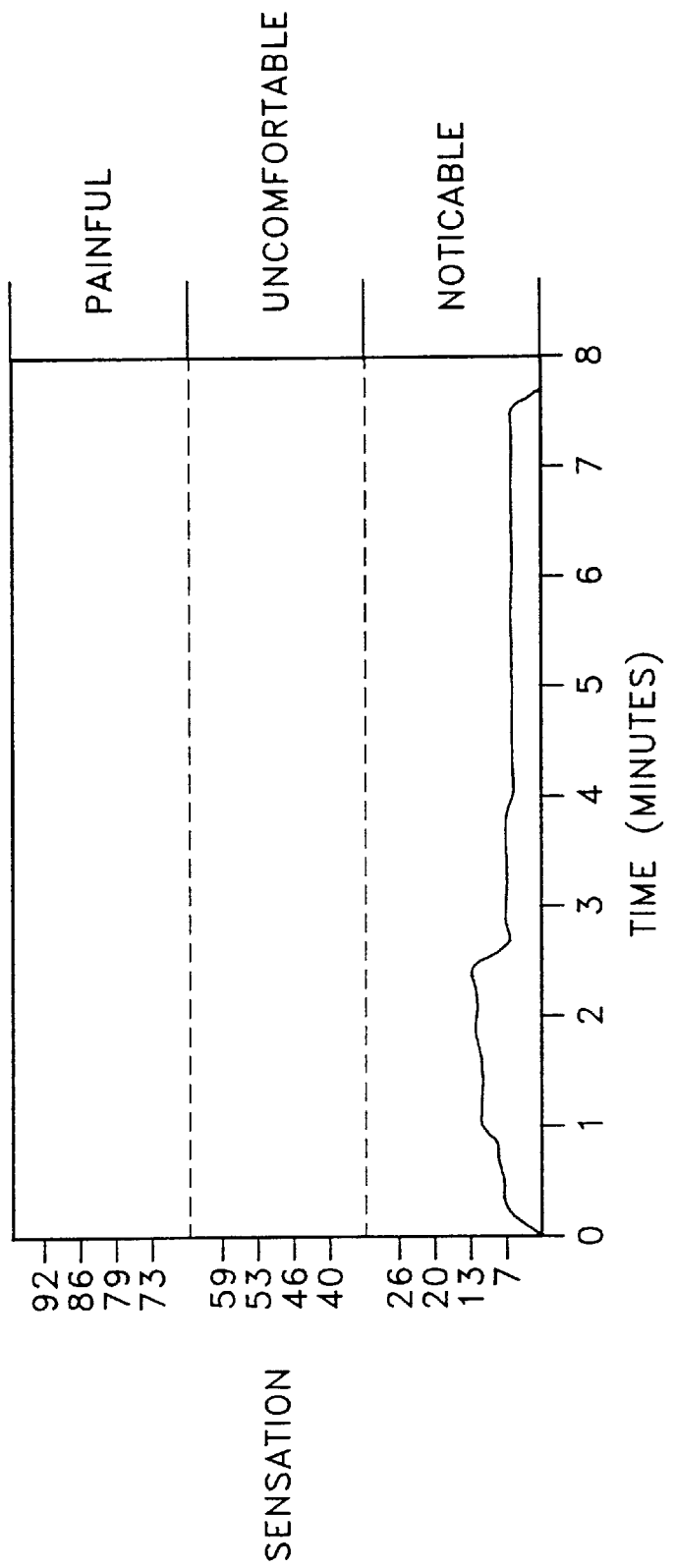
Figure 5B:
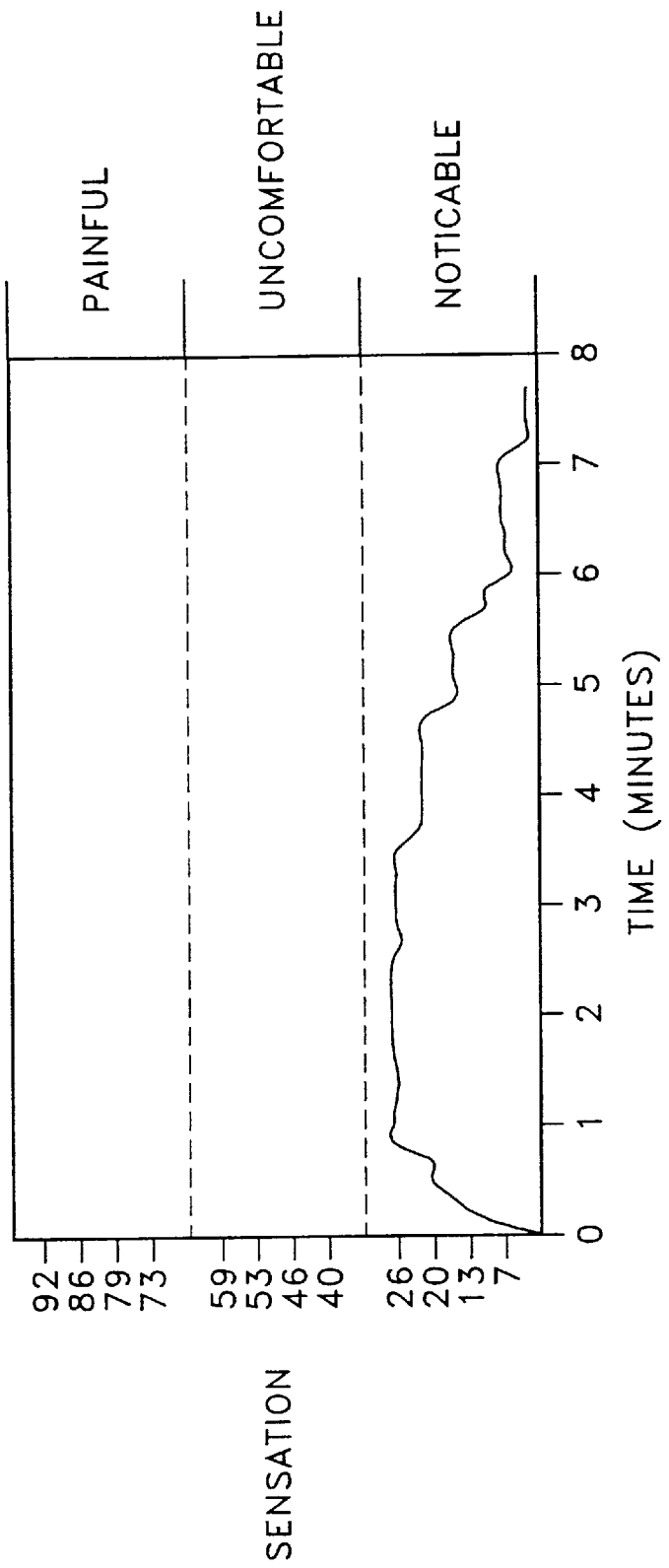
Figure 6B:
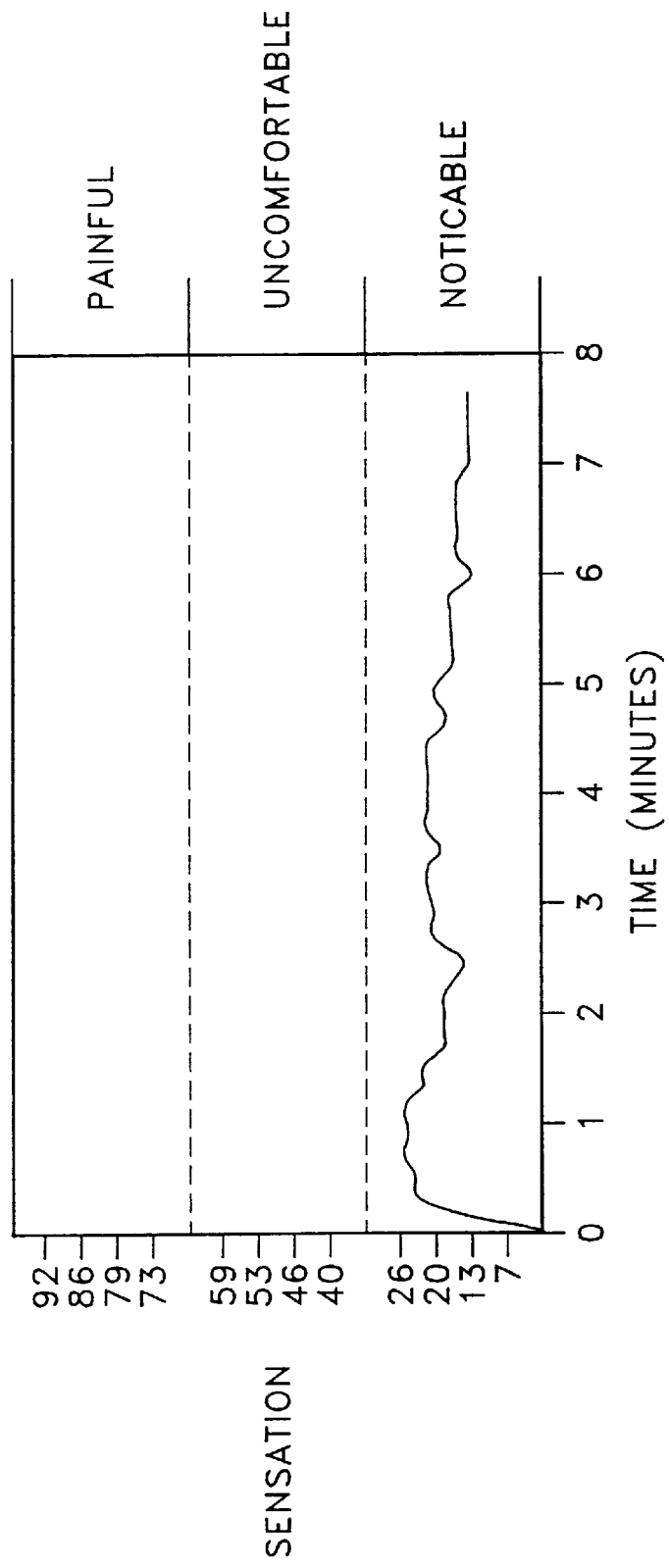
Figure 7:
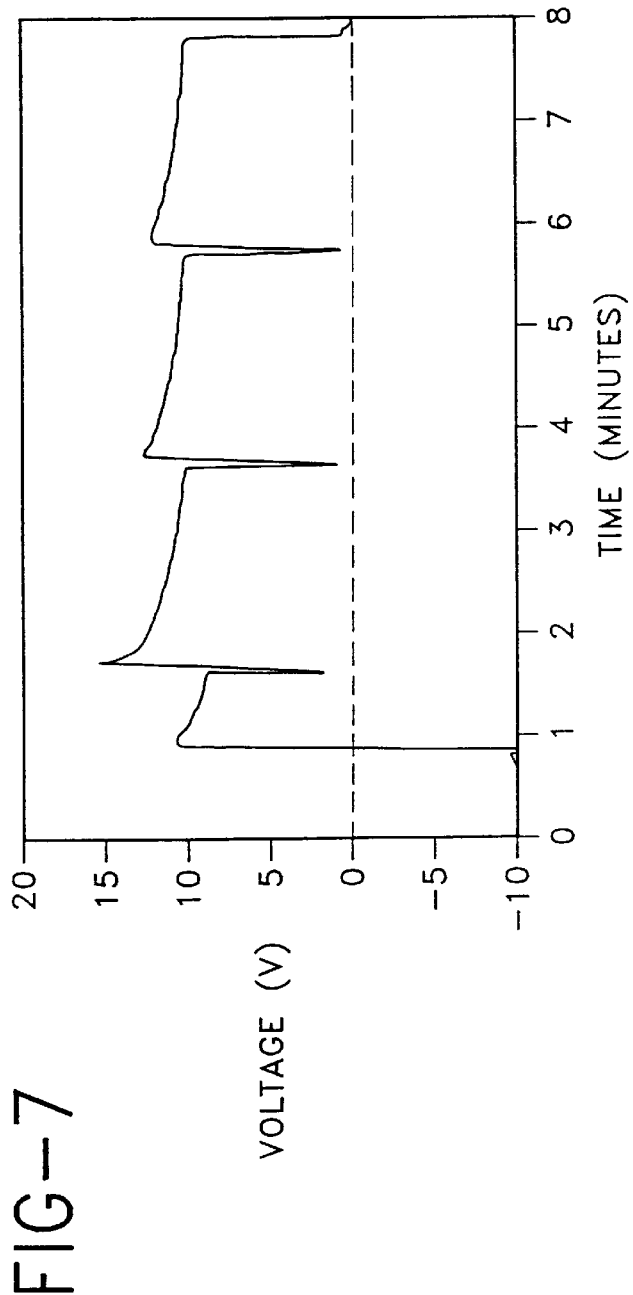
FIGS. 7, 7A and 7B are a set of graphs showing current sensation of the two electrode embodiment of the present invention wherein the current is reversed after an initial period of time (minutes) and the Voltage (V) is on the average at about 10 volts and the Current is then increased to values higher than 0.5 mA.
Figure 7A:
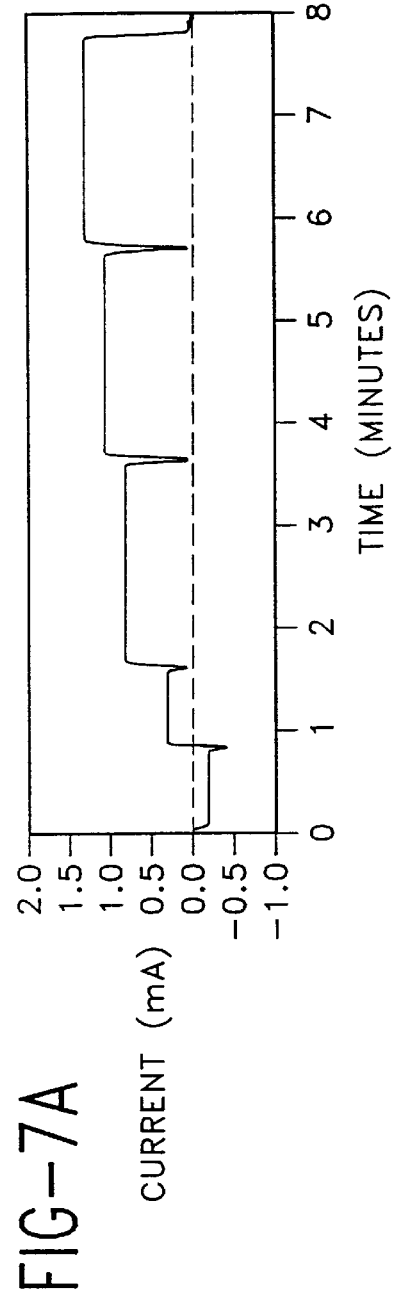
Figure 7B:
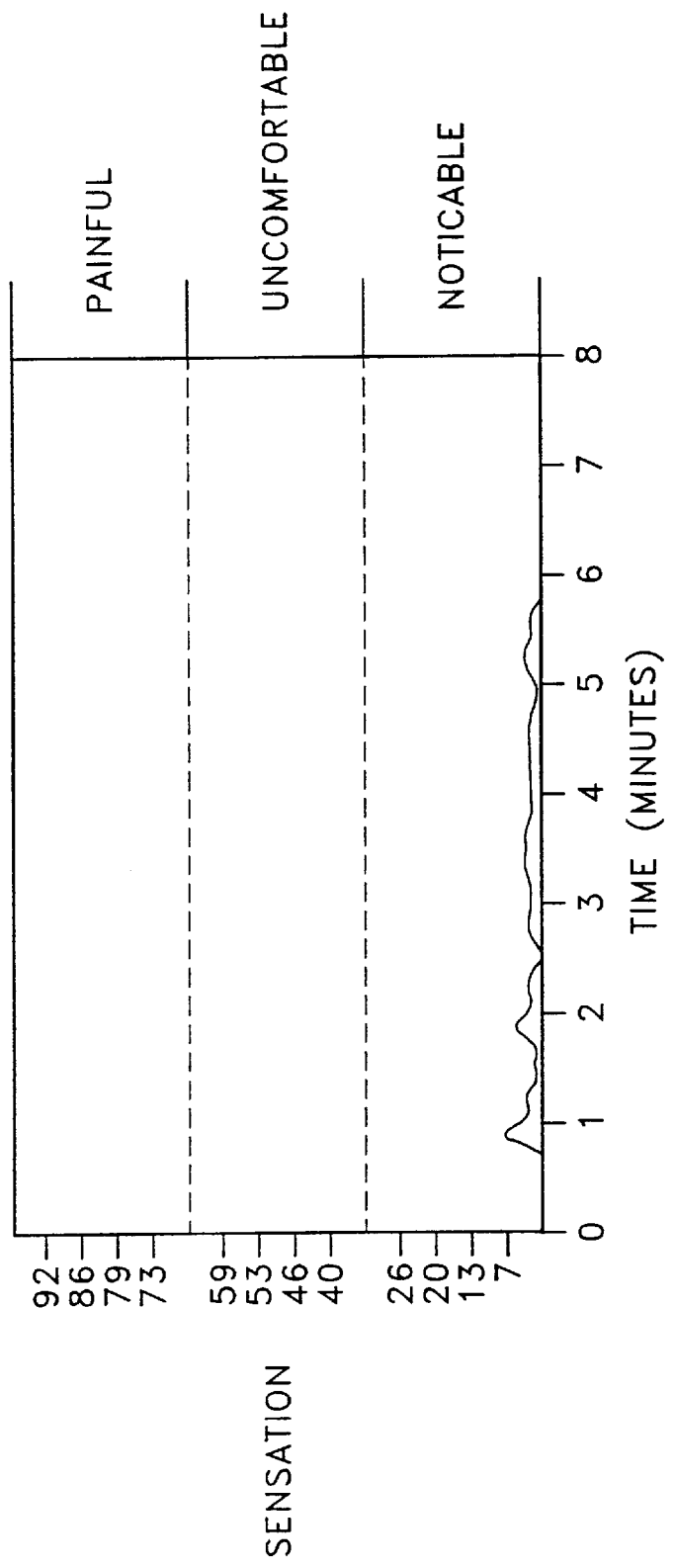
Figure 8B:
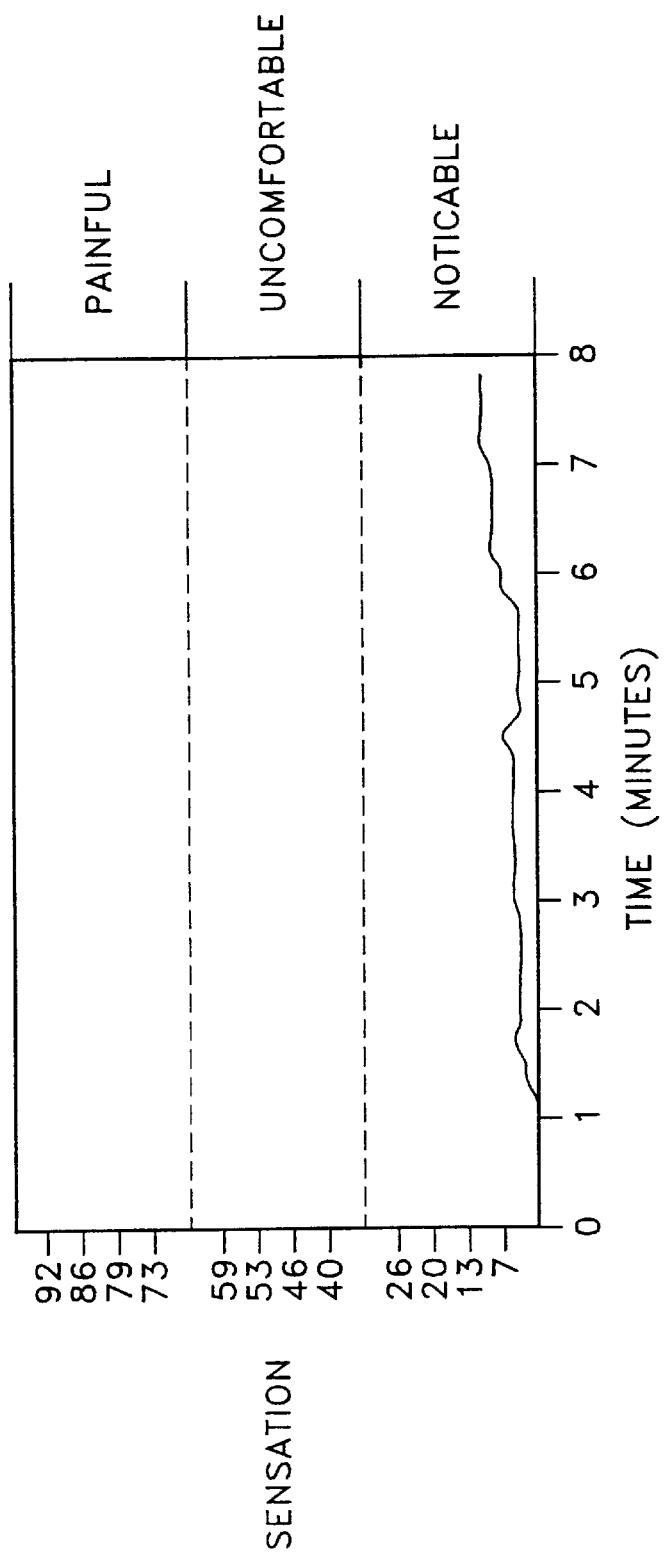
Figure 9B:
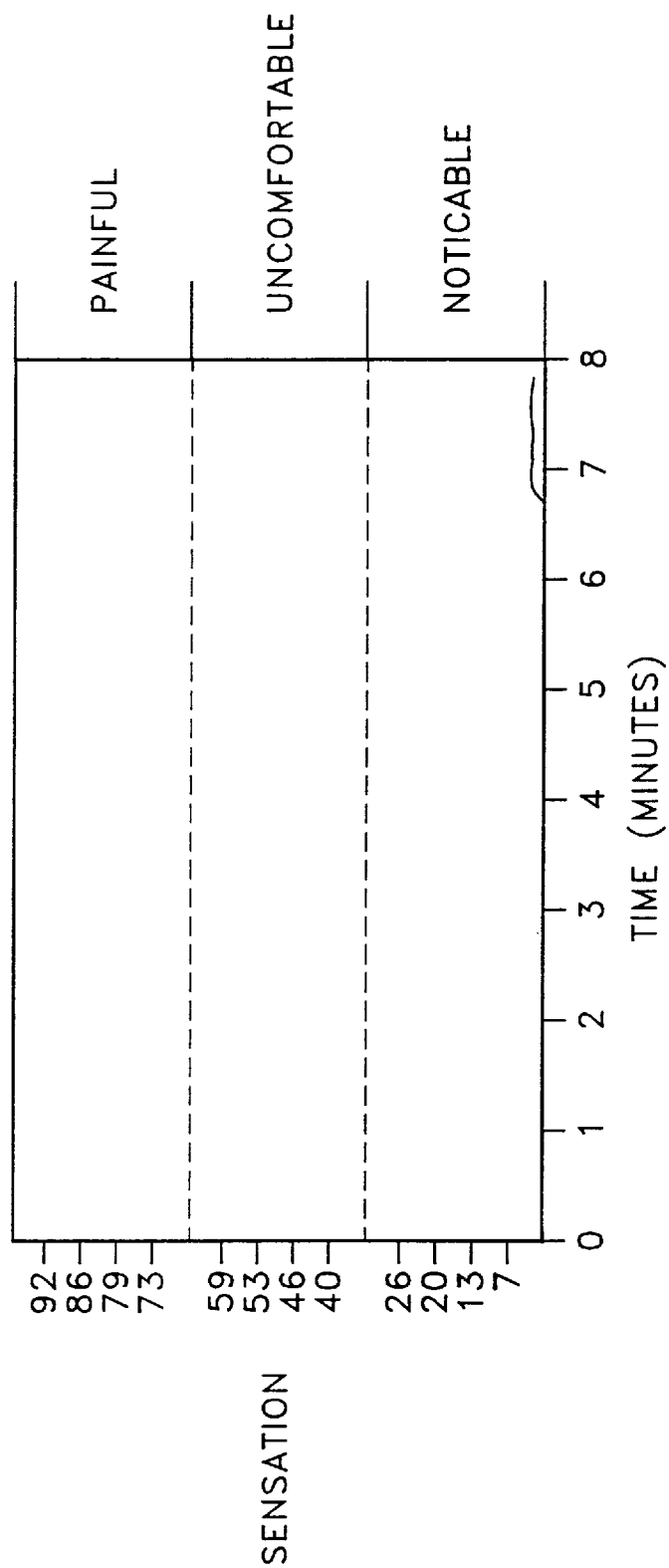

In the three electrode embodiment of the present invention, as illustrated in FIGS. 1A, 2B and 3A, where the active agent contained in the reservoirs 34, 44 is positively charged, the electrical current flows from the first electrode 32 to the third electrode 52 during a first time period and the first electrode 32 acts as the active electrode and the third electrode 52 acts as the return electrode, with the drug 26 being delivered to the applied area of the skin approximate the first electrode 32 and first reservoir 34.

In either embodiment of the present invention, after the elapse of a predetermined period of time $(T_1)$, the flow of electrical current is reversed or switched so that it flows from the second electrode 42 through second reservoir 44 to the first electrode 32 during a second time period $(T_2)$ in which the second electrode 42 acts as the active electrode and the first electrode 32 acts as the return electrode. In this way, the active agent 26 is delivered to the applied area of the skin approximate the second electrode 42 and the second reservoir 44.

FIGS. 4, 4A, 4B–9, 9A and 9B are sets of graphs showing current delivery and resulting sensation as recorded by a VAS (Visual-Analog-Scale) in connection with experiments representing iontophoretically transported Lidocaine (a local anesthetic) and Epinephrine (a vasoconstrictor), with FIGS. 4, 4A, 4B–6, 6A and 6B showing direct current baselines and FIGS. 7, 7A, 7B–9, 9A and 9B showing the results with polarity reversal. Along the horizontal axis of each graph is shown time in minutes, along the vertical axis of each top graph is shown the voltage in volts (V), along the vertical axis of each middle graph is shown the current in milliamperes (mA), and along the vertical axis of each bottom graph is shown the sensation assessment of human volunteers using the device 20 of the present invention.

The significant area of the graphs is plotted in the bottom graphs, with the baseline areas (direct current) being compared with the areas for the graphs representing the experiments with the claimed invention (reversed polarity) wherein the local anesthetic and the vasoconstrictor were iontophoretically delivered. Accordingly, looking at the data, the device 20 can be used to administer a local anesthetic in as little as eight minutes with the first period of time not exceeding one minute and the second period of time not exceeding seven minutes, utilizing up to approximately 1.5 mA of current with little if any sensation, whereas sensations are much higher at ⅓ the current without the benefit of current reversal.

Experiments were conducted on volunteers using the following formulations in connection with the two electrode embodiment of device 20 of the present invention illustrated in FIGS. 1, 2, 2A and 3:

EXAMPLE 1

As shown in FIGS. 4, 4A, 4B–9, 9A and 9B, 15% (150 mgm/ML) of Lidocaine HCl (local anesthetic) and 45 μgm Epinephrine (vasoconstrictor), on a dry web activated when the moisture from the reservoirs came in contract with the web, were used for anesthetizing the applied area to minimize sensation from the insertion of a needle or the like. The Epinephrine was utilized in combination with the Lidocaine to limit or otherwise restrict the Lidocaine formulation from being drawn away from the applied area by the vasculature. In this way, the Epinephrine was delivered first since it was also positively charged and was already in contact with the skin. However, it should be appreciated that the Lidocaine and the Epinephrine could be contained in the reservoirs in solutions.

The results of the experiments illustrated in FIGS. 4, 4A, 4B–6, 6A and 6B were conducted with only one of the reservoirs including the Lidocaine formulation and the Epinephrine to establish a baseline. However, the results of the experiments illustrated in FIGS. 7, 7A, 7B–9, 9A and 9B were conducted with both reservoirs including the Lidocaine formulation and the use of Epinephrine.

As is readily apparent, when the Lidocaine is delivered through the cathode first by reversing the current at current levels less than 500 uA for a sufficient period of time, enough anesthetic was delivered to deaden the nerves to subsequent higher currents. Accordingly, when the current was reversed, the current was able to be increased to a much higher level with out the volunteers feeling much sensation. However, initially after reversal, the current must again be kept at a level low enough and long enough at the true anode to allow the anesthetic to take effect, then the current can be increased to the level necessary to completely anesthetize the area under the anode. Most sensations produced by the ion flow into the cathode previously experienced and reflected in FIGS. 4, 4A, 4B–6, 6A and 6B is blocked by the small amount of anesthetic initially delivered under the cathode as reflected in FIGS. 7, 7A, 7B–9, 9A and 9B.

In addition, it should be appreciated that other formulations including Lidocaine HCl in the range of 5% w/v–15% w/v and Epinephrine in the range of 0.03% w/v–3.0% w/v may be utilized.

While the above-described example illustrates the use of the two electrode embodiment of the present invention, the same formulations and parameters can be used with the three electrode embodiment of device 20 of the present invention.

Active agent, drug, formulation, medication, medicament and active compound have been used herein to mean any pharmaceutical agent, such as therapeutic compounds, diagnostic agents, anesthetic agents and the like.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

While the preferred embodiments of the present invention has been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

We claim:

1. A method of reducing sensation in as little as eight minutes during rapid iontophoretic delivery of at least a local anesthetic to an applied area of a patient such as the skin, comprising the steps of:

applying a first portion of an iontophoretic drug delivery device including an electrode assembly having a first electrode and a first reservoir containing at least a local anesthetic to be delivered to the applied area of the patient;

applying a second portion of the device including said electrode assembly having a second electrode and a second reservoir containing said at least a local anesthetic to be delivered to the applied area of the patient;

generating an electrical current between said first electrode and said second electrode through the applied area of the patient in a first direction during a first period of time less than one minute at low current so that at least enough of said local anesthetic is delivered to the applied area of the patient approximate said first electrode and said first reservoir to anesthetize the applied area approximate said first electrode and said first reservoir at least sufficiently to avoid sensation due to electrical current flowing through the applied area of the patient approximate thereto; and reversing the direction of said electrical current through the applied area of the patient in a second direction and generating an electrical current between said second electrode and said first electrode during a second period of time less than seven minute so that during said second period of time a higher current is provided for a longer period of time to said second electrode to deliver said local anesthetic to anesthetize the applied area of the patient approximate said second electrode without unwanted sensation due to electrical current flowing through the applied area of the patient and to minimize sensation from the subsequent insertion of a needle or the like into the applied area of the patient.

2. A method of reducing sensation as defined in claim 1, wherein a vasoconstrictor is delivered along with said local anesthetic.

3. A method of reducing sensation as defined in claim 2, wherein said local anesthetic is Lidocaine and said vasoconstrictor is Epinephrine.

4. A method of reducing sensation as defined in claim 1, further comprising the step of varying the amount of electrical current.

5. A method of reducing sensation as defined in claim 1, wherein said step of generating an electrical current in said first direction during said first period of time includes limiting the amount of electrical current delivered to at least initially less than or equal to 0.5 mA.

6. A method of reducing sensation as defined in claim 5, wherein said step of generating electrical current in said second direction during said second period of time includes limiting the amount of electrical current delivered to at least initially less than or equal to 0.5 mA.

7. A method of reducing sensation as defined in claim 6, further comprising the step of generating an electrical current in said second direction for at least one additional period of time during which the amount of electrical current delivered is greater than 0.5 mA.

8. A method of reducing sensation as defined in claim 7, wherein the amount of electrical current delivered during said at least one additional period of time is in the range of approximately 0.05 mA to 1.5 mA.

9. A method of reducing sensation as defined in claim 8, wherein the amount of electrical current delivered during said first period of time is limited to a low current of at least initially less than or equal to 0.5 mA, and wherein the amount of electrical current delivered during said second direction during said second period of time is limited to a low current of at least initially less than or equal to 0.5 mA and then the amount of electrical current delivered is raised to at a higher current greater than 0.5 mA so as to minimize sensation from the subsequent insertion of a needle or the like into said applied area.

* * * * *